(12) United States Patent
Watanabe

(10) Patent No.: US 7,604,796 B2
(45) Date of Patent: Oct. 20, 2009

(54) HAIR CLEANSING COMPOSITIONS

(75) Inventor: Shunsuke Watanabe, Tokyo (JP)

(73) Assignee: Kao Corporation, Tokyo (JP)

( * ) Notice: Subject to any disclaimer, the term of this patent is extended or adjusted under 35 U.S.C. 154(b) by 773 days.

(21) Appl. No.: 11/020,293

(22) Filed: Dec. 27, 2004

(65) Prior Publication Data

US 2005/0142090 A1    Jun. 30, 2005

(30) Foreign Application Priority Data

Dec. 26, 2003    (JP) ............................ 2003-431725

(51) Int. Cl.
*A61Q 5/02* (2006.01)

(52) U.S. Cl. .............. 424/70.19; 424/70.11; 424/70.21; 424/70.24; 424/70.31

(58) Field of Classification Search ........................ None
See application file for complete search history.

(56) References Cited

U.S. PATENT DOCUMENTS

| 4,240,450 | A | 12/1980 | Grollier et al. |
| 4,445,521 | A | 5/1984 | Grollier et al. |
| 4,597,962 | A | 7/1986 | Grollier et al. |
| 4,719,099 | A | 1/1988 | Grollier et al. |
| 5,009,880 | A | 4/1991 | Grollier et al. |
| 5,609,861 | A | 3/1997 | Dubief et al. |
| 2003/0198615 | A1 * | 10/2003 | Wong et al. .............. 424/70.12 |

FOREIGN PATENT DOCUMENTS

| EP | 1 118 319 A1 | 7/2001 |
| JP | 59-187095 | 10/1984 |
| WO | WO 99/55295 | 11/1999 |
| WO | WO 01/78670 A2 | 10/2001 |
| WO | WO 01/78671 A2 | 10/2001 |
| WO | WO 03/055457 A1 | 7/2003 |

* cited by examiner

*Primary Examiner*—Jyothsna A Venkat
(74) *Attorney, Agent, or Firm*—Oblon, Spivak, McClelland, Maier & Neustadt, L.L.P.

(57) ABSTRACT

A hair cleansing composition contains (A) from 10 to 20 wt % of at least one surfactant selected from the group consisting of anionic surfactants, nonionic surfactants and amphoteric surfactants; (B) from 1 to 8 wt % of a multivalent, water-soluble, inorganic salt; (C) from 0.1 to 2 wt % of a cationic polymer; and (D) from 5 to 20 wt % of a polyhydric alcohol. As a method for preventing colored hair from fading, shampooing of the colored hair is performed with the hair cleansing composition. The hair cleansing composition of the present invention inhibits the bleeding of a colorant from the colored hair through shampooing, shows good lathering and gives a smooth touch feel upon shampooing, leaves no stiff feeling after drying, and is excellent in stability.

6 Claims, No Drawings

HAIR CLEANSING COMPOSITIONS

FIELD OF THE INVENTION

This invention relates to hair cleansing compositions containing a surfactant and a multivalent, water-soluble, inorganic salt, which inhibit the bleeding of a colorant from the colored hair through shampooing, show good lathering, give a smooth touch feel upon shampooing, leave no stiff feeling after drying, and have excellent stability.

BACKGROUND OF THE INVENTION

Changing of the hair color of a person by coloring can alter his or her impression by making him or her look young and/or cheerful. The colored hair is, however, accompanied by a problem that its color quickly fades through degradation or deterioration of the colorant by ultraviolet rays or oxidation or through bleeding of the colorant by repeated use of shampoo, hair treatment and/or the like.

To prevent such fading, a UV absorber or antioxidant is generally incorporated in a hair cleansing composition. Mere incorporation of such a UV absorber or the like, however, is not sufficient to prevent this fading. For the purpose of preventing the bleeding of a colorant during shampooing, there have been proposed cleansing compositions with a silicone incorporated therein to coat the hair surface (U.S. Pat. No. 5,609,861 and U.S. Patent Application Publication No. 2003/0198615A). It is, however, difficult to effectively coat the interface between hair and water with a silicone or the like upon shampooing. With a view toward replenishing a colorant which bleeds, there have also been proposed shampoos and conditioners with the colorant incorporated therein directly (the international publication WO 03/055457, 01/78670 and 01/78671). These shampoos and conditioners, however, have not succeeded in fully satisfying consumers due to reasons such as the hair color obtained after the shampooing becomes different from the original hair color imparted by the coloring or the colorant deposits in the skin or transfers to a towel, pillow case or the like.

SUMMARY OF THE INVENTION

In one aspect of the present invention, there is provided a hair cleansing composition containing the following ingredients (A) to (D):

(A) from 10 to 20 wt % of at least one surfactant selected from the group consisting of anionic surfactants, nonionic surfactants and amphoteric surfactants;
(B) from 1 to 8 wt % of a multivalent, water-soluble, inorganic salt;
(C) from 0.1 to 2 wt % of a cationic polymer; and
(D) from 5 to 20 wt % of a polyhydric alcohol.

In another aspect of the present invention, there is also provided a method for preventing colored hair from fading, which contains performing shampooing of the colored hair with the above-described hair cleansing composition.

DETAILED DESCRIPTION OF THE INVENTION

This invention relates to hair cleansing compositions, which can inhibit the bleeding of a colorant from the colored hair through shampooing, show good lathering, give a smooth touch feel upon shampooing, leave no stiff feeling after drying, and are excellent in stability.

The present inventors have found that a hair cleansing composition, which meets the above-described requirements, can be obtained by incorporating specific amounts of a multivalent, water-soluble, inorganic salt, cationic polymer and polyhydric alcohol in a hair cleansing composition.

As the ingredient (A), i.e., the anionic surfactant, a sulfate-type anionic surfactant is preferred. Specific examples include polyoxyethylene alkyl ether sulfates, polyoxyethylene alkenyl ether sulfates, alkyl sulfates, and polyoxyalkylene alkyl phenyl ether sulfates. Among these, anionic surfactants represented by the following formula (1) or (2) are preferred:

$$R^1O(CH_2CH_2O)_mSO_3M \tag{1}$$

$$R^2OSO_3M \tag{2}$$

wherein $R^1$ represents an alkyl group or alkenyl group having 10 to 18 carbon atoms, $R^2$ represents an alkyl group having 10 to 18 carbon atoms, M represents an alkali metal, alkaline earth metal, ammonium, alkanolamine or basic amino acid, and m stands for a number of from 1 to 5 on weight average.

Two or more of these anionic surfactants can be used in combination. From the standpoint of the stability of the hair cleansing composition, its liquid properties and ease of lathering at the time of use and its ease of shampooing during use, the content of the anionic surfactant may range preferably from 1 to 19 wt %, more preferably from 5 to 18 wt %, even more preferably from 10 to 17 wt %.

Examples of the nonionic surfactants include polyoxyalkylene sorbitan fatty acid esters, polyoxyalkylene sorbitol fatty acid esters, polyoxyalkylene glycerol fatty acid esters, polyoxyalkylene fatty acid esters, polyoxyalkylene alkyl ethers, polyoxyalkylene alkyl phenyl ethers, polyoxyalkylene (hydrogenated) castor oils, sucrose fatty acid esters, polyglyceryl alkyl ethers, polyglyceryl fatty acid esters, fatty acid alkanolamides, and alkyl glycosides. Among these, alkyl glycosides, polyoxyalkylene ($C_8$-$C_{20}$) fatty acid esters, polyoxyethylene sorbitan fatty acid esters, polyoxyethylene hydrogenated castor oil and fatty acid alkanolamides are preferred. Preferred fatty acid alkanolamides are those containing acyl groups having from 8 to 18, more preferably from 10 to 16 carbon atoms. The fatty acid alkanolamides can be either monoalkanolamides or dialkanolamides. Preferred are those containing hydroxyalkyl groups having from 2 to 3 carbon atoms. Illustrative are oleic diethanolamide, palm kernel oil fatty acid diethanolamide, coconut oil fatty acid diethanolamide, lauric diethanolamide, polyoxyethylene coconut oil fatty acid monoethanolamides, coconut oil fatty acid monoethanolamides, lauric isopropanolamide, and lauric monoethanolamide.

Two or more of these nonionic surfactants can be used in combination. From the standpoint of the stability of the hair cleansing composition, its liquid properties and ease of lathering at the time of use, its ease of shampooing during use and the assurance of fine and soft foam quality, the content of the nonionic surfactant may range preferably from 0.1 to 10 wt %, more preferably from 0.2 to 7 wt %, even more preferably from 0.5 to 5 wt %.

The amphoteric surfactants can include betaine-type surfactants. Among these, betaine-type surfactants such as alkyldimethylaminoacetic acid betaines, alkylcarboxylmethylhydroxyethylimidazoliniuim betaines and fatty acid amidopropyl betaines are more preferred, with fatty acid amidopropyl betaines being more preferred. Of these fatty acid amidopropyl betaines, preferred are those having acyl groups having from 8 to 18 carbon atoms, especially from 10 to 16 carbon atoms. Specifically, lauramidopropyl betaine, palm kernel oil fatty acid amidopropyl betaines, coconut oil fatty acid amidopropyl betaines and the like are preferred.

Two or more of these amphoteric surfactants can be used in combination. From the standpoint of the stability of the hair cleansing composition, its liquid properties and ease of lathering at the time of use, its ease of shampooing during use and the assurance of fine and soft foam quality, the content of the amphoteric surfactant may range preferably from 0.1 to 10 wt %, more preferably from 0.2 to 7 wt %, even more preferably from 0.5 to 5 wt %.

The total content of the surfactant (A) amounts to from 10 to 20 wt %, preferably from 11 to 19 wt %, more preferably from 12 to 18 wt % of the hair cleansing composition of the present invention. From the standpoint of improved cleansing property and lathering power and adequate liquid properties, it is preferred to use a nonionic surfactant or amphoteric surfactant in combination with a sulfate-type anionic surfactant, with the combined use of a polyoxyalkylene alkyl ether, fatty acid amidopropyl betaine or fatty acid alkanolamide in combination with a polyoxyethylene alkyl ether sulfate or alkyl sulfate being more preferred. From the standpoint of foam-boosting effect for the cleansing composition, the content weight ratio of the polyoxyethylene alkyl ether sulfate or alkyl sulfate to the polyoxyalkylene alkyl ether, fatty acid amidopropyl betaine or fatty acid alkanolamide may range preferably from 1:1 to 50:1, more preferably from 3:1 to 30:1, even more preferably from 5:1 to 15:1.

Concerning the multivalent, water-soluble, inorganic salt as the ingredient (B), the term "multivalent" means that its cation and/or anion group is multivalent. Examples are inorganic salts (sulfates, sulfites, phosphates, phosphites) composed of multivalent anions such as sulfate ions, sulfite ions, phosphate ions and phosphite ions, and monovalent or multivalent cations; or inorganic salts composed of multivalent cations, such as alkaline earth metal ions, aluminum ions and heavy metal ions, and monovalent anions.

Dyes employed in hair colors generally include oxidation dyes, acidic dyes and basic dyes, and preferably, oxidation dyes are used in common. As these dyes readily disperse and dissolve in water, they tend to bleed by regular shampooing even when the hair is once dyed with them. As a method for inhibiting the bleeding of such a dye, it may be contemplated to lower the dispersibility and solubility of the dye in water. In a state that the dye is dispersed and dissolved in water (a colloidal dispersion of the dye), the dye has been provided with high dispersibility owing to its hydration and surface charges of the colloidal dye. Neutralization of the surface charges are, therefore, considered to lower the water dispersibility of the dye, and as a result, to inhibit the fading of the colored hair by shampooing. It is, therefore, considered that the use of multivalent ions makes it possible to efficiently neutralize the surface charges of the colloidal dye.

The polarity of effective multivalent ions depends upon the surface charges of the corresponding colloidal dye. Oxidation dyes which are used in common are of the amine type, and are considered to have positive surface charges under the shampooing pH condition, that is, in the range of from neutral to weak acidity. Preferred examples of the multivalent, water-soluble, inorganic salt, therefore, include sulfates, sulfites and phosphates, with sulfates being more preferred. Examples of cations which form such inorganic salts include monovalent ions such as lithium ion, potassium ion and sodium ion, and multivalent ions such as calcium ion and magnesium ion. A monovalent cation, specifically sodium ion is preferred especially when an anionic surfactant is contained.

Specific examples of the sulfates include disodium sulfate, sodium hydrogen sulfate and potassium sulfate. Specific examples of the sulfites include sodium sulfite and potassium sulfite. Specific examples of the phosphates include trisodium phosphate, disodium hydrogen phosphate, sodium dihydrogenphosphate and tripotassium phosphate. Among these, sodium sulfate is preferred.

From the standpoint of raising the concentration of the multivalent, water-soluble, inorganic salt in water to reduce dissolution and bleeding of the colorant contained inside the hair into water upon shampooing and the stability of the cleansing composition, the content of the ingredient (B) is from 1 to 8 wt %, preferably from 2 to 6 wt %, more preferably from 3 to 4 wt % in the hair cleansing composition of the present invention.

Examples of the cationic polymer as the ingredient (C) include cationized cellulose derivatives, cationic starch, cationized guar gum derivatives, homopolymer of diallyl quaternary ammonium salt, diallyl quaternary ammonium salt/acrylamide copolymer, quaternized polyvinyl-pyrrolidone derivatives, polyglycol polyamine condensation products, vinylimidazolium trichloride/vinylpyrrolidone copolymer, hydroxyethylcellulose/dimethyldiallylammonium chloride copolymer, vinylpyrrolidone/quaternized dimethylaminoethyl methacrylate copolymer, polyvinylpyrrolidone/alkyl aminoacrylate copolymer, polyvinylpyrrolidone/alkyl aminoacrylate/vinyl caprolactam copolymers, vinylpyrrolidone/methacrylamidopropyl trimethylammonium chloride copolymer, alkylacrylamide/acrylate/alkylaminoalkylacrylamide/polyethylene glycol methacrylate copolymers, adipic acid/dimethylaminohydroxypropyl ethylenetriamine copolymer ("CARTARETIN"; product of Sandoz Chemicals Corp., U.S.A.), and cationic polymers disclosed in JP-A-53139734 and JP-A-60036407. Among these, preferred are cationized cellulose derivatives, cationized guar gum derivatives, and diallyl quaternary ammonium salt/acrylamide copolymers.

Two or more of these cationic polymers can be used in combination. From the standpoint of controlling liquid properties of the hair cleansing composition, provision of fine, soft and long-lasting foam quality and smoothness from the time of lathering to the time of rinsing, and manageability ease of the hair after drying, the content of the cationic polymer is from 0.1 to 2 wt %, preferably from 0.2 to 1.5 wt %, more preferably from 0.3 to 1 wt %.

Examples of the polyhydric alcohol as the ingredient (D) include glycols having two hydroxyl groups, glycerins having three hydroxyl groups, and in addition, condensation products of saccharides, glycols and glycerins. Specifically, ethylene glycol, propylene glycol, 1,2-butylene glycol, 1,3-butylene glycol, 3-methyl-1,3-butylene glycol, dipropylene glycol, hexylene glycol, glycerin, trimethylolpropane, pentaerythritol, xylitol, sorbitol, mannitol and the like are preferred. More preferred are propylene glycol and glycerin, with glycerin being even more preferred.

Two or more of these polyhydric alcohols can be used in combination. From the standpoint of inhibiting bleeding of the colorant from the inside of the hair and the assurance of fine foams, the content of the polyhydric alcohols is from 5 to 20 wt %, preferably from 8 to 15 wt %. Further, the weight ratio of the ingredient (A) to the ingredient (D) may be preferably from 4:1 to 1:2, more preferably from 3:1 to 1:1.5, even more preferably from 2:1 to 1:1.

In the hair cleansing composition of the present invention, a nonionic polymer can be incorporated further as an ingredient (E). Examples of the nonionic polymer include polyvinylpyrrolidone, hydroxyethylcellulose, and polyvinyl alcohol. Among these, polyvinyl alcohol is preferred. From the standpoint of the assurance of fine foams, the polyvinyl alcohol may preferably have an average polymerization degree of from 500 to 5,000, with a range of from 1,000 to 4,000 being more preferred. Also from the standpoint of the assurance of fine foams, its saponification degree may preferably range from 65 to 90, with a range of from 70 to 85 being more preferred. Two or more nonionic polymers can be used in combination. From the standpoints of foam-quality improving effects, controlling and stability of liquid properties of the composition and the like, the content of the nonionic polymer is preferably from 0.01 to 1 wt %, more preferably from 0.05 to 0.75 wt %, even more preferably from 0.1 to 0.5 wt %.

From the standpoint of inhibiting the degradation or deterioration of the colorant existing inside the hair after coloring to prevent its fading and also inhibiting the bleeding of the colorant by the deterioration of damages of the hair itself, an oil-soluble or water-soluble UV absorber can be also incorporated as an ingredient (F). Examples of the oil-soluble UV absorber include those of the benzoic acid type, the anthranilic acid type, the salicylic acid type, the cinnamic acid type, and the benzophenone type. Examples include, as UV absorbers of the benzoic acid type, p-aminobenzoic acid (hereinafter abbreviated as "PABA"), ethyl p-aminobenzoate, glyceryl PABA, ethyldihydroxypropyl PABA, ethyl N-ethoxylate-PABA, ethyl N-dimethyl-PABA, butyl N-dimethyl-PABA, amyl N-dimethyl-PABA, and octyl dimethyl PABA; as a UV absorber of the anthranilic acid type, homomenthyl N-acetylanthranilate; as UV absorbers of the salicylic acid type, amyl salicylate, menthyl salicylate, homomenthyl salicylate, octyl salicylate, phenyl salicylate, benzyl salicylate, and p-isopropanolphenyl salicylate; as UW absorbers of the cinnamic acid type, octyl cinnamate, ethyl 4-isopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, 2-ethylhexyl p-methoxycinnamate, 2-ethoxyethyl p-methoxycinnamate, cyclohexyl p-methoxycinnamate, ethyl α-cyano-β-phenylcinnamate, 2-ethylhexyl α-cyano-β-phenylcinnamate, and glyceryl mono-2-ethylhexanoyl diparamethoxycinnamate; as UV absorbers of the benzophenone type, 2,4-dihydroxybenzophenone, 2,2'-dihydroxy-4-methoxybenzophenone, 2,2'-dihydroxy-4,4'-dihydroxybenzophenone, 2-hydroxy-4-methoxybenzophenone, 2-hydroxy-4-methoxy-4'-methylbenzophenone, 2-hydroxy-4-methoxybenzophenone, 4-phenylbenzophenone, 2-ethylhexyl-4'-phenylbenzophenone-2-carboxylate, 2-hydroxy-4-n-octoxybenzophenone, 4-hydroxy-3-carboxybenzophenone, and 4-t-butyl-4'-methoxydibenzoylmethane.

Examples of the water-soluble UV absorber include diethanolamine p-methoxycinnamate, sodium 2-hydroxy-4-methoxybenzophenone-5-sulfonate, tetrahydroxybenzophenone, methylherperidin, sodium 3-hydroxy-4-methoxycinnamate, sodium ferulate, 2-phenylbenzimidazole-5-sulfonic acid ("EUSOLEX™"; product of Merck & Co., Ltd.), and urocanic acid. Animal or plant extracts having UV absorbing effect can also be mentioned such as milfoil (*Achillea milleforium*), aloe, witch hazel, hamamelis, burdock, and sage. Among these, 2-ethoxyethyl p-methoxycinnamate and 2-hydroxy-4-methoxybenzophenone are preferred, with 2-ethoxyethyl p-methoxycinnamate being more preferred.

The content of the UV absorber may be preferably from 0.01 to 1 wt %, more preferably from 0.02 to 0.8 wt %, even more preferably from 0.05 to 0.5 wt %, all based on the hair cleansing composition of the present invention.

Similar to the incorporation of the UV absorber, an antioxidant may also be incorporated further as an ingredient (G) in the hair cleansing composition of the present invention to inhibit the degradation of the colorant existing inside the hair, to prevent the bleeding and fading of the colorant and to inhibit the bleeding of the colorant as a result of damages to the hair. Examples of the antioxidant include vitamin E, vitamin E derivatives, vitamin C, cysteine, butylhydroxyanisole, butylhydroxytoluene, gallic acid, propyl gallate, erthorbic acid, erthorbate salts, sulfites, and hydrogensulfites. Among these, vitamin E and vitamin E derivatives are preferred. Examples of vitamin E derivatives include DL-α-tocopherol, DL-α-tocopherol acetate, and DL-α-tocopherol nicotinate.

The content of the antioxidant may be preferably from 0.01 to 1 wt %, more preferably from 0.02 to 0.8 wt %, even more preferably from 0.05 to 0.5 wt %, all based on the hair cleansing composition of the present invention.

In the hair cleansing composition of the present invention, one or more of conditioning ingredients such as silicones, oil ingredients and cationic surfactants can be incorporated further to improve the post-drying finish. Examples of the silicones can include the followings:

(Silicones—Category 1) Dimethylpolysiloxanes

Examples are those represented by the following formula (3):

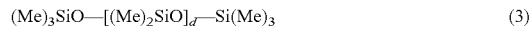

$$(Me)_3SiO-[(Me)_2SiO]_d-Si(Me)_3 \qquad (3)$$

wherein each Me represents a methyl group, and d stands for a number of from 3 to 20,000.

(Silicones—Category 2) Amino-Modified Silicones

One having an average molecular weight of from about 3,000 to 100,000 and listed under the name of "Amodimethicone" in the third edition of the CTFA dictionary (Cosmetic Ingredient Dictionary, U.S.A.) is preferred, although a variety of amino-modified silicones are usable. This amino-modified silicone can be used preferably as an aqueous emulsion, and its commercial products include "SM 8704C" (trade name, Dow Corning Toray Silicone Co., Ltd.) and "DC 929" (trade name, Dow Corning Corporation).

(Silicones—Category 3) Other Silicones

As silicones other than those described above, there may be polyether-modified silicones, methylphenylpolysiloxane, fatty-acid-modified silicones, alcohol-modified silicones, alkoxy-modified silicones, epoxy-modified silicones, fluorine-modified silicones, cyclic silicones, alkyl-modified silicones, and the like.

Two or more of these silicones may be used in combination. From the standpoint of improvements in post-drying silkiness, finger-combing ease and sleekness, the content of the silicone may be preferably from 0.1 to 7 wt %, more preferably from 0.2 to 6 wt %, even more preferably from 0.5 to 5 wt %, all based on the hair cleansing composition of the present invention.

Examples of the oil ingredients include hydrocarbons such as squalene, squalane, liquid paraffin, liquid isoparaffin and cycloparaffin; glycerides such as castor oil, cacao oil, mink oil, avocado oil, and olive oil; waxes such as beeswax, whale wax, lanolin, and carnauba wax; alcohols such as myristyl alcohol, cetyl alcohol, oleyl alcohol, stearyl alcohol, isostearyl alcohol, and 2-octyldodecanol; esters such as isopropyl palmitate, isopropyl myristate, octyldecyl myristate, hexyl laurate, cetyl lactate, propylene glycol monostearate, oleyl oleate, hexadecyl 2-ethylhexanoate, isononyl isononanoate, and tridecyl isononanoate; higher fatty acids such as capric acid, lauric acid, myristic acid, palmitic acid, stearic acid, behenic acid, oleic acid, coconut oil fatty acids, isostearic acid, and isopalmitic acid; isostearyl glyceryl ethers; and polyoxypropylene butyl ether. Of these, esters are preferred, with hexadecyl 2-ethylhexanoate, isononyl isononanoate and isopropyl palmitate being more preferred.

Two or more of these oil ingredients may be used in combination. From the standpoint of improvements in post-drying silkiness, finger-combing ease and sleekness, the content of the oil ingredient may be preferably from 0.1 to 7 wt %, more preferably from 0.2 to 6 wt %, even more preferably from 0.5 to 5 wt %, all based on the hair cleansing composition of the present invention.

Example of the cationic surfactants include lauryltrimethylammonium chloride, cetyltrimethylammonium chloride, cetyltrimethylammonium bromide, stearyltrimethylammonium chloride, stearyltrimethylammonium bromide, laurylt-rimethylammonium bromide, dialkyldimethylammonium chlorides, dicetyldimethylammonium chloride, distearyldimethylammonium chloride, dicocoyldimethylammonium chloride, myristyldimethylbenzylammonium chloride, stearyldimethylbenzylammonium chloride, lanolin fatty acid aminopropylethyldimethylammonium ethyl sulfate, lanolin fatty acid aminoethyltriethylammonium ethyl sulfate, lanolin fatty acid aminoethyldiethylmethylammonium ethyl sulfate, lanolin fatty acid aminoethyltrimethylammonium methyl sulfate, lanolin fatty acid aminopropylethyltriethylammonium ethyl sulfate, lanolin fatty acid aminoethyltrimethylammonium methyl sulfate, lanolin fatty acid aminopropylethyldimethylammonium methyl sulfate, isoalkanoic acid ($C_{14}$-$C_{20}$) aminopropylethyldimethylammonium ethyl sulfate, isoalkanoic acid ($C_{18}$-$C_{22}$) aminopropylethyldimethylammonium ethyl sulfate, isostearic acid aminopropylethyldimethylammonium ethyl sulfate, isononanoic acid aminopropylethyldimethyl ammonium ethyl sulfate, and alkyltrimethylammonium saccharins.

Two or more of these cationic surfactants may be used in combination. From the standpoint of improvements in post-drying silkiness, finger-combing ease and sleekness, the content of the cationic surfactant may be preferably from 0.1 to 10 wt %, more preferably from 0.2 to 7 wt %, even more preferably from 0.5 to 5 wt %, all based on the hair cleansing composition of the present invention.

From the standpoint of imparting pearlescence, the hair cleansing composition of the present invention may additionally contain a pearlant. Examples of the pearlant include dialkyl ethers and ethylene glycol dialkyl ethers, each of which contains alkyl groups having 18 to 22 carbon atoms per group; and ethylene glycol mono (fatty acid) esters, ethylene glycol di (fatty acid) esters, fatty acid monoethanolamides and acylated β-alanines, each of which has an acyl group having 18 to 22 carbon atoms. Two or more of these pearlants may be used in combination. The content of the pearlant may be preferably from 0.05 to 10 wt %, more preferably from 0.1 to 5 wt %, even more preferably from 0.5 to 1 wt %, all based on the hair cleansing composition of the present invention.

The hair cleansing composition of the present invention may additionally contain a glyceryl ether having 1 to 3 linear or branched alkyl or alkenyl groups with 4 to 12 carbon atoms per group. Among such glyceryl ethers, preferred are those containing 1 to 3 alkyl groups having 4 to 12 carbon atoms per group such as n-butyl, isobutyl, t-butyl, n-pentyl, isopentyl, n-hexyl, isohexyl, n-heptyl, n-octyl, 2-ethylhexyl, n-nonyl, n-decyl, isodecyl or n-dodecyl groups. More preferred are those containing 1 to 3 alkyl groups having 4 to 11, preferably 8 to 10 carbon atoms per group. Even more preferred are those containing one or two, preferably one of such alkyl groups. Two or more of these glyceryl ethers may be used in combination. From the standpoint of assuring good foam quality, adequate liquid properties and good stability, the content of such a glyceryl ether may be preferably from 0.1 to 10 wt %, more preferably from 0.4 to 5 wt %, even more preferably from 1 to 5 wt %, all based on the hair cleansing composition of the present invention.

In addition to the above-described ingredients, ingredients which are employed in ordinary hair cleansing compositions can also be incorporated in the hair cleansing composition of the present invention as needed depending upon the purpose of use. Such ingredients include, for example, antidandruff agents; vitamins; antifungal agents; antimicrobial agents; anti-inflammatories; preservatives; chelating agents; humectants such as sorbitol and panthenol; pigments; viscosity controlling agents such as hydroxyethylcellulose, methylcellulose, polyethylene glycol, and clay mineral; pH adjusters including organic acids, such as lactic acid, citric acid and malic acid, and potassium hydroxide; plant extracts; pearlants such as titanium oxide; fragrances; colorants; and other ingredients described in ENCYCLOPEDIA OF SHAMPOO INGREDIENTS (MICELLE PRESS).

The form of the hair cleansing composition of the present invention can be chosen as desired, which includes a liquid form, a powder form, a gel form, and a granular form. However, a liquid form making use of water or a lower alcohol as a solvent is preferred, with a liquid form making use of water as a solvent being more preferred.

EXAMPLES

The present invention will hereinafter be described more specifically based on examples. It is, however, to be noted that the present invention shall not be limited to the following examples.

Examples 1-7 and Comparative Examples 1-5

The hair cleansing compositions shown in Table 5 were each formulated, and by the testing methods to be described below, ranked for the bleeding of its colorant from hair, its external appearance shortly after its formulation, its storage stability, the smoothness of hair upon rinsing, and the non-stiffness of hair after drying.

(Bleeding of the Colorant from Hair)

(1) Preparation of Colored Tresses

Each tress was prepared by precisely weighing out 2.5 g of Caucasian light-brown hair of about 20 cm in length with no history of chemical treatments such as a permanent wave and binding the cuticle end with a glue.

The bleach packs 1 and 2 shown in Table 1 were weighed out as much as 2.5 g each, combined into a uniform mixture, and then evenly applied onto the tress. After the tress was left at room temperature for 30 minutes, it was rinsed with running water and then dried by a dryer.

Subsequently, the hair color packs 1 and 2 shown in Table 2 were weighed out as much as 2.5 g each, combined into a uniform mixture, and then evenly applied onto the tress. The tress was left at room temperature for 30 minutes. While rinsing the tress with running water, the tress was then shampooed once with the model shampoo (0.2 g) shown in Table 3, and the model conditioner (0.2 g) shown in Table 4 was applied to soak into the tress thoroughly. The tress was then dried by a dryer.

TABLE 1

| Ingredients | wt % |
|---|---|
| Model Bleach Pack 1 | |
| Aqueous ammonia (28 wt %) | 10 |
| Ammonium hydrogencarbonate | 15 |
| Purified water | Balance |
| Model Bleach Pack 2 | |
| Hydrogen peroxide solution (35 wt %) | 15 |
| Cetanol | 2.5 |
| Strearyltrimethylammonium chloride (63 wt %) | 4 |
| Hydroxyquinoline sulfate | 0.05 |
| Phosphoric acid | Sufficient to adjust the pH to 3.5 |
| Fragrance | 0.5 |
| Purified water | Balance |

TABLE 2

| Ingredients | wt % |
|---|---|
| Model Hair Color Pack 1 | |
| Aqueous ammonia (28 wt %) | 5.0 |
| Monoethanolamine | 2.0 |
| Cetanol | 8.5 |
| 2-Methyl-5-hydroxyethylaminophenol | 0.4 |
| 4-Amino-2-hydroxytoluene | 0.3 |
| Paraaminophenol | 0.3 |
| Phenylenediamine | 0.3 |
| Resorcinol | 0.01 |
| POE(40) cetyl ether | 3.0 |
| POE(2) cetyl ether | 3.5 |
| Stearyltrimethylammonium chloride | 2.0 |
| Liquid paraffin | 0.5 |
| Sodium sulfite | 0.5 |
| Ascorbic acid | 0.5 |
| Tetrasodium edetate | 0.1 |
| Fragrance | 0.4 |
| Ammonium chloride | Sufficient to adjust the pH to 10 |
| Purified water | Balance |
| Model Hair Color Pack 2 | |
| Hydrogen peroxide solution (35 wt %) | 17.0 |
| Phosphoric acid | Sufficient to adjust the pH to 3.5 |
| Purified water | Balance |

TABLE 3

| Ingredients | wt % |
|---|---|
| Model Shampoo | |
| Sodium lauryl ether sulfate | 17.0 |
| Lauric diethanolamide | 2.0 |
| Fragrance | 0.5 |
| Citric acid | Sufficient to adjust the pH to 6 |
| Purified water | Balance |

TABLE 4

| Ingredients | wt % |
|---|---|
| Model Conditioner | |
| Behenyltrimethylammonium chloride | 0.8 |
| Stearyl alcohol | 2.5 |
| Fragrance | 0.3 |
| Purified water | Balance |

(2) Colorant Bleeding Test

The colored tress (2.5 g) was dipped in a beaker which contained water (70 g), and was then pulled out. While catching dripping water in the beaker, one (0.2 g) of the hair cleansing compositions shown in Table 5 was applied. While making the tress extend straight with fingers, the colored tress was rubbed up and down 30 times with fingers over 30 seconds such that the hair cleansing composition thoroughly soaked into the colored tress. With the hair cleansing composition kept applied on the colored tress, the colored tress was dipped in the beaker and rinsed there for 30 seconds. Subsequently, water was squeezed off with fingers and caught in the beaker. Another beaker with water (70 g) placed therein was newly provided, and the tress was rinsed again for 30 seconds in the beaker. Water was squeezed off in a similar manner, and the tress was dried by a dryer.

The above-described operation was repeated 7 times so that 14 washing-containing beakers were obtained. The washings in the thus-obtained 14 beakers were individually subjected to centrifugation at 3,000 rpm for 2 hours. With respect to each washing, its supernatant was collected and then filtered through a cellulose acetate filter (pore size: 0.45 μm). The absorbance of the filtrate at 475 nm was measured. The absorbance was measured with a 1 cm×1 cm cell by using a spectrophotometer "DU650" (trade name; manufactured by BECKMAN INSTRUMENTS, INC.). Employed as a reference upon performing the measurement was a filtrate of a washing obtained by conducting similar treatments on a tress which was similar to the above tress except that the coloring alone was not applied. The total value of 60 absorbance data so obtained was recorded as an index of the amount of bled colorant.

(External Appearance of Hair Cleansing Composition Shortly after its Formulation)

The external appearance of each hair cleansing composition shortly after its formulation was ranked in accordance with the following standards:

Ranking standards

A: clear

B: semi-clear

C: cloudy (Storage Stability)

Each hair cleansing composition was sealed in a glass sample bottle. After being stored for 6 days under conditions involving temperature variations (25° C.→60° C.→25° C.→15° C.→25° C. was set as a cycle per day), the hair cleansing composition was observed for coloration, gelation and the like, and its stability was ranked in accordance with the following standards:

Ranking Standards

A: not changed

B: changed

C: clearly separated (Smoothness of Hair upon Rinsing, and Non-Stiffness of Hair after Drying)

Using the tresses, their smoothness upon rinsing and their non-stiffness after drying were ranked. The ranking was performed by five expert panelists, and the ranking results are indicated by average scores.

Ranking standards
3: very good
2: good
1: cannot be said either
0: bad

TABLE 5

| Ingredients (wt %) | Examples | | | | | | | Comparative Examples | | | | |
|---|---|---|---|---|---|---|---|---|---|---|---|---|
| | 1 | 2 | 3 | 4 | 5 | 6 | 7 | 1 | 2 | 3 | 4 | 5 |
| Sodium lauryl ether sulfate (2EO) | 12.6 | 12.6 | 12.6 | 12.6 | 12.6 | 12.6 | 12.6 | 12.6 | 12.6 | 12.6 | 12.6 | 12.6 |
| Sodium lauryl sulfate | 1.2 | 1.2 | 1.2 | 1.2 | 1.2 | 1.2 | 1.2 | 1.2 | 1.2 | 1.2 | 1.2 | 1.2 |
| Lauramidopropyl betaine | 1.5 | 1.5 | 1.5 | 1.5 | 1.5 | 1.5 | 1.5 | 1.5 | 1.5 | 1.5 | 1.5 | 1.5 |
| POE(16) lauryl ether | 1 | 1 | 1 | 1 | 1 | 1 | 1 | 1 | 1 | 1 | 1 | 1 |
| Lauric acid | 0.5 | 0.5 | 0.5 | 0.5 | 0.5 | 0.5 | 0.5 | 0.5 | 0.5 | 0.5 | 0.5 | 0.5 |
| Cationized cellulose* | 0.5 | 0.5 | 0.5 | 0.5 | 0.5 | 0.5 | 0.5 | 0.5 | 0.5 | 0.5 | 0.5 | 0.5 |
| Polyvinyl alcohol** | 0.2 | 0.2 | 0.2 | 0.2 | 0.2 | 0.2 | 0.2 | 0.2 | 0.2 | 0.2 | 0.2 | 0.2 |
| Glycerin | 10 | 10 | 10 | 10 | 10 | 10 | 10 | 10 | 10 | 10 | 10 | 10 |
| Sodium sulfate | 1 | 2 | 3 | 4 | 6 | 8 | — | — | 0.1 | 0.5 | 10 | — |
| Magnesium sulfate | — | — | — | — | — | — | 3 | — | — | — | — | — |
| Sodium chloride | — | — | — | — | — | — | — | — | — | — | — | 3 |
| Fragrance | — | — | — | — | — | — | 0.5 | — | — | — | — | 0.5 |
| Purified water | Bal | Bal | Bal | Bal | Bal | Bal | Bal | Bal | Bal | Bal | Bal | Bal |
| Bleeding of colorant from hair | 0.55 | 0.47 | 0.47 | 0.51 | 0.50 | 0.52 | 0.45 | 0.72 | 0.77 | 0.78 | 0.50 | 0.77 |
| External appearance shortly after formulation | A | A | A | A | B | C | A | A | A | A | C | A |
| Storage stability | A | A | A | A | A | A | B | A | A | A | C | A |
| Smoothness of hair upon rinsing | 2.0 | 2.4 | 2.6 | 2.4 | 2.4 | 2.4 | 2.0 | 2.0 | 2.0 | 2.2 | 2.6 | 2.4 |
| Non-stiffness of hair after drying | 2.4 | 2.6 | 2.4 | 2.4 | 2.4 | 2.0 | 2.0 | 2.0 | 2.0 | 2.0 | 1.6 | 2.0 |

*"POLYMER JR 30M" (trade name; product of Amerchol Corporation
**"CELVOL ™ -205S" (product of Celanese AG)

Example 8

Clear Shampoo

| | (wt %) |
|---|---|
| Sodium polyoxyethylene lauryl sulfate | 12.0 |
| Sodium lauryl sulfate | 1.0 |
| Lauramidopropyl betaine | 1.0 |
| POE(16) lauryl ether | 1.0 |
| Glyceryl monoisodecyl ether | 0.5 |
| Cationized cellulose ("POLYMER JR 30M", trade name; product of Amerchol Corporation) | 0.5 |
| Polyvinyl alcohol ("CELVOL ™ -205S"; product of Celanese AG) | 0.2 |
| Glycerin | 10.0 |
| Sodium sulfate | 3.0 |
| Tocopherol acetate | 0.2 |
| 2-Ethylhexyl paramethoxycinnamate | 0.1 |
| 2-Hydroxy-4-methoxybenzophenone | 0.1 |
| Fragrance | 0.1 |
| Sodium hydroxide | Sufficient to give pH 7 |
| Purified water | Balance |

Example 9

Pearlescent Shampoo

| | (wt %) |
|---|---|
| Sodium polyoxyethylene lauryl sulfate | 12.0 |
| Sodium lauryl sulfate | 1.0 |

-continued

| | (wt %) |
|---|---|
| Sodium cocoamphoacetate | 1.0 |
| POE(16) lauryl ether | 1.0 |
| Myristic acid | 0.5 |
| Cationized guar gum ("RHABALL ™ GUM CG-M7L"; product of Dainippon Pharmaceutical Co., Ltd.) | 0.5 |
| Ethylene glycol distearate | 1.0 |
| Silicone emulsion ("J POVAL JL25E; trade name; product of JAPAN VAM & POVAL CO., LTD.) | 2.0 |
| Polyvinyl alcohol ("CELVOL ™-205S"; product of Celanese AG) | 0.2 |
| Glycerin | 10.0 |
| Sodium sulfate | 3.0 |
| Tocopherol acetate | 0.2 |
| 2-Ethylhexyl paramethoxycinnamate | 0.1 |
| 2-Hydroxy-4-methoxybenzophenone | 0.1 |
| Fragrance | 0.1 |
| Sodium hydroxide | Sufficient to give pH 7 |
| Purified water | Balance |

I claim:

1. A one-part hair cleansing composition comprising the following ingredients (A) to (D):
    (A) from 12 to 18 sodium lauryl ether sulfate (2EO) and sodium lauryl and lauramidopropyl betaine and POE (16) lauryl ether;
    (B) from 3 to 4 wt % of a sodium sulfate;
    (C) from 0.3 to 1 wt % of a cationized cellulose; and
    (D) from 8 to 15 wt % of a glycerin.

2. The hair cleansing composition according to claim 1, further comprising, as an ingredient (B), from 0.01 to 1 wt % of a nonionic polymer.

3. The hair cleansing composition according to claim 1, further comprising, as an ingredient (F), from 0.01 to 1 wt % of a UV absorber.

4. The hair cleansing composition according to claim 1, further comprising, as an ingredient (G), from 0.01 to 1 wt % of an antioxidant.

5. A method for treating colored hair from fading, which comprises performing shampooing of said colored hair with one part a hair cleansing composition as defined in claim 1.

6. The hair cleansing composition according to claim 1, wherein the composition does not contain a colorant.

* * * * *

UNITED STATES PATENT AND TRADEMARK OFFICE
CERTIFICATE OF CORRECTION

| | | |
|---|---|---|
| PATENT NO. | : 7,604,796 B2 | Page 1 of 1 |
| APPLICATION NO. | : 11/020293 | |
| DATED | : October 20, 2009 | |
| INVENTOR(S) | : Shunsuke Watanabe | |

It is certified that error appears in the above-identified patent and that said Letters Patent is hereby corrected as shown below:

Title page, item (*) Notice: should read as follows: Subject to any disclaimer, the term of this patent is extended or adjusted under 35 U.S.C. 154(b) by 1240 days.

Column 13, line 4, "from 12 to 18 sodium lauryl" should read --from 12 to 18 wt% of sodium lauryl--;

line 11, "ingredient (B)" should read --ingredient (E)--.

Column 14, line 9, "one part a hair cleansing" should read --an one-part hair cleansing--.

Signed and Sealed this

Seventh Day of September, 2010

David J. Kappos
*Director of the United States Patent and Trademark Office*